United States Patent
Kintzig et al.

(10) Patent No.: US 8,974,384 B2
(45) Date of Patent: Mar. 10, 2015

(54) DATA PROCESSING DEVICE FOR PROCESSING MEASURED VALUES

(75) Inventors: Hans Kintzig, Tiefenthal (DE); Ulrich Porsch, Weinheim (DE); Christian Blatt, Neckarsteinach (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 1330 days.

(21) Appl. No.: 12/020,674

(22) Filed: Jan. 28, 2008

(65) Prior Publication Data

US 2008/0243758 A1    Oct. 2, 2008

(30) Foreign Application Priority Data

Jan. 31, 2007 (EP) ..................... 07002063

(51) Int. Cl.
*A61B 5/00* (2006.01)
*A61B 5/15* (2006.01)
(Continued)

(52) U.S. Cl.
CPC ............. *A61B 5/0002* (2013.01); *A61B 5/1411* (2013.01); *A61B 5/14532* (2013.01); *A61B 5/6887* (2013.01); *G06F 19/3406* (2013.01)
USPC ........................................ 600/300

(58) Field of Classification Search
CPC ... G10L 15/26; G10L 15/1822; G10L 17/005; G10L 21/0208; G10L 13/00; G10L 13/02; G10L 15/00; G10L 17/06; G10L 19/018; G10L 2021/02165; G10L 2025/783; G10L 21/00; G10L 21/02; G10L 21/038; G10L 25/51; G10L 25/78; G10L 25/90; G10L 19/008; G10L 19/0212; G10L 19/09; G10L 19/265; G10L 2021/0135; G10L 21/0272; G10L 25/18; G10L 17/00; G10L 17/26; G10L 19/00; G10L 19/0017; H04R 1/1041; H04R 1/1066; H04R 2420/07; H04R 5/0335; H04R 1/1025; H04R 1/1083; H04R 2201/103; H04R 2460/13; H04R 1/105; H04R 2499/11; G02C 11/06; G09B 21/001; G09B 21/006; G09B 21/007; G09B 21/008; H04S 7/303; A61B 5/6803; A61B 5/145; A61B 5/14532; A61B 5/4803; G06Q 50/24

See application file for complete search history.

(56) References Cited

U.S. PATENT DOCUMENTS 3,827,041 A    7/1974 Cook
4,637,403 A *  1/1987 Garcia et al. .................. 600/583

(Continued)

FOREIGN PATENT DOCUMENTS

DE    102004057503 A1    6/2006
EP         0293958 B1    7/1991

(Continued)

OTHER PUBLICATIONS

Uslan et al. Accessibility of Blood Glucose Monitoring Systems for Blind and Visually Impaired People, Diabetes Technology & Therapeutics vol. 5, No. 3, 2003.*

*Primary Examiner* — Gary Jackson
*Assistant Examiner* — Shirley Jian
(74) *Attorney, Agent, or Firm* — Roche Diagnostics Operations, Inc.

(57) ABSTRACT

A data processing device is provided for processing measurement values provided from a medical measurement device. The device generally comprises an input unit, a data input interface configured for communication with the medical measurement device, a memory unit for storage of data sets, a calculation unit, and an audible data output interface configured for communication with a data output unit. The input unit is configured for making a first selection of the data sets stored in the memory unit. Second selections based on or within the first selection may also be made. The audible data output interface is provided for generating an audible output of the selected data sets. The audible data output interface may also be configured to generate distinct audible signals before the audible output of each different selection of data sets.

26 Claims, 1 Drawing Sheet

(51) Int. Cl.
*A61B 5/145* (2006.01)
*G06F 19/00* (2011.01)

(56) References Cited

U.S. PATENT DOCUMENTS

| | | | |
|---|---|---|---|
| 4,653,100 A | 3/1987 | Barnett et al. | |
| 5,787,411 A | 7/1998 | Groff et al. | |
| 6,052,108 A | 4/2000 | Gadd | |
| 6,115,482 A * | 9/2000 | Sears et al. | 382/114 |
| 6,379,301 B1 * | 4/2002 | Worthington et al. | 600/309 |
| 6,790,178 B1 * | 9/2004 | Mault et al. | 600/300 |
| D555,708 S * | 11/2007 | Cheng | D16/330 |
| 7,445,332 B2 * | 11/2008 | Jannard et al. | 351/158 |
| 7,452,073 B2 * | 11/2008 | Jannard et al. | 351/158 |
| 7,461,936 B2 * | 12/2008 | Jannard | 351/158 |
| 7,494,216 B2 * | 2/2009 | Jannard et al. | 351/158 |
| 7,512,414 B2 * | 3/2009 | Jannard et al. | 455/556.1 |
| 7,682,018 B2 * | 3/2010 | Jannard | 351/158 |
| 7,740,353 B2 * | 6/2010 | Jannard | 351/158 |
| 7,744,213 B2 * | 6/2010 | Jannard et al. | 351/158 |
| 7,967,433 B2 * | 6/2011 | Jannard et al. | 351/158 |
| 7,988,283 B2 * | 8/2011 | Jannard | 351/158 |
| 8,010,156 B2 * | 8/2011 | Warren | 455/556.1 |
| 8,020,989 B2 * | 9/2011 | Jannard et al. | 351/158 |
| 8,025,398 B2 * | 9/2011 | Jannard | 351/158 |
| 8,313,192 B2 * | 11/2012 | Jannard | 351/158 |
| 8,473,004 B2 * | 6/2013 | Warren | 455/556.1 |
| 8,482,488 B2 * | 7/2013 | Jannard | 345/8 |
| 8,523,352 B2 * | 9/2013 | Jannard et al. | 351/158 |
| 8,545,013 B2 * | 10/2013 | Hwang et al. | 351/158 |
| 8,550,621 B2 * | 10/2013 | Jannard | 351/158 |
| 8,787,970 B2 * | 7/2014 | Warren | 455/556.1 |
| 8,876,285 B2 * | 11/2014 | Jannard | 351/158 |
| 2002/0133627 A1 | 9/2002 | Maes et al. | |
| 2004/0016802 A1 | 1/2004 | Cummings | |
| 2004/0156012 A1 * | 8/2004 | Jannard et al. | 351/158 |
| 2004/0157649 A1 * | 8/2004 | Jannard et al. | 455/569.1 |
| 2005/0089150 A1 | 4/2005 | Birkhead et al. | |
| 2005/0159656 A1 | 7/2005 | Hockersmith et al. | |
| 2005/0201585 A1 | 9/2005 | Jannard et al. | |
| 2006/0132382 A1 * | 6/2006 | Jannard | 345/8 |
| 2006/0197907 A1 * | 9/2006 | Jannard et al. | 351/158 |
| 2009/0187407 A1 * | 7/2009 | Soble et al. | 704/260 |

FOREIGN PATENT DOCUMENTS

| | | |
|---|---|---|
| EP | 0 607 727 A1 | 7/1994 |
| EP | 1369688 A2 | 12/2003 |
| EP | 1372102 A2 | 12/2003 |
| EP | 1559364 A1 | 8/2005 |
| EP | 1 674 975 A2 | 6/2006 |
| EP | 1728470 A1 | 12/2006 |
| EP | 1 769 963 A2 | 4/2007 |
| EP | 1933300 A1 | 6/2008 |
| WO | 2007/005170 A2 | 1/2007 |

* cited by examiner

DATA PROCESSING DEVICE FOR PROCESSING MEASURED VALUES

PRIORITY CLAIM

The present application is based on and claims the priority benefit of European Patent Application No. 07002063.1, filed Jan. 31, 2007, which is hereby incorporated by reference in its entirety.

TECHNICAL FIELD OF THE INVENTION

The present invention relates to a data processing device for processing measured values and a method for operating a data processing device. In particular, the present invention relates to a data processing device four the audible output of medically relevant data.

BACKGROUND OF THE INVENTION

In the medical field it is common for portable patient devices to be deployed for collecting patient data. These portable devices are often connected to central data processing devices, in which the monitoring, selection, analysis etc. of the data is performed either by medical personnel, doctors or even automatically. Such portable devices are deployed, among other things, to collect and monitor blood glucose levels from diabetics. From EP 1 559 364 A1 for example, a wireless diabetes monitoring system is known, in which the patients are informed of their results via mobile phone after their blood glucose levels have been transmitted to a control centre. A further comparable system is known from US 2005/0089150 A1, wherein, via telephone and portable apparatus, an interactive briefing of a user/patient takes place by means of a voice recognition system and software generated instructions to the user.

People suffering from diabetes mellitus have to strive to keep their blood glucose value within a particular range at all times. If the desired range is exceeded, insulins needs to be injected. If the desired range is undershot, glucose needs to be administered orally (by means of food or a drink). If the desired range is exceeded over a relatively long time, there is the risk of serious health complications, such as visual impairment (e.g. blindness), kidney damage, mortification of limbs or neuropathy. If the range is exceeded significantly for a short time, this may result in nausea, dizziness, sweating and even states of confusion. If the desired range is undershot significantly for a short time, this may likewise result in nausea, dizziness, sweating, confusion and—in the worst case—the death of the diabetic. It is therefore absolutely imperative for a diabetic to know the generally status of his blood glucose at all times and if necessary to be able to initiate suitable measures independently in order to prevent the blood glucose value from breaking out of the desired range. To this end, blood glucose measuring devices have already been used for some time, such as are known from DE 10 2004 057 503 A1 and sold by the applicant under the registered trade mark ACCU-CHEK®. Ideally, the diabetic handles measurement of the blood glucose value and the measurement results himself.

The blood glucose level is subject to severe fluctuation, depending on the insulin administration (as a general rule, differently acting insulins can be used at the same time), on the ingested sugar quantity and other foods and fluids which physiologically affect the glucose metabolism. Additionally affecting the glucose metabolism are physical activity, stress, illness, etc. Because not every organism reacts in the same way to these physiological parameters, every diabetic must get to know his own physiological reactions. For this reason, it is essential to maintain a diabetes-diary. Using the entries recorded in such a written diary, the diabetic can search for similar situations in his past entries and compare with the current situation, in order to then take corresponding measures to induce a correction in his metabolism. As a result of the diary entries, he is in a position to repeat successful correction of the metabolism, or to provide a better correction to the physiological situation than in the past through appropriate adjustments to the corrective action if the correction in the similar situation did not provide the desired result. Therefore, as already mentioned, a serious need arises for each diabetic to maintain such a diary in which all parameters and corrective actions of the metabolism-control cycle are noted.

Around 80% of all visually impaired (e.g. blind) diabetics are visually impaired as a result of diabetes, i.e. the blood glucose of these people was not at the correct level for a long time, which led to visual impairment. Because of their visual impairment, these diabetics are unable to maintain a diary for themselves, as previously described, and until now they have not been in a position to independently administer insulin therapy. Although care through other people is possible, experience shows that the blood glucose level of the visually impaired patient is worse in that case than when he independently regulates his own blood glucose; i.e. independent regulation of one's own blood glucose reduces the risk of further health related complications.

Visually impaired and visually impaired (partially visually impaired) diabetics therefore have a great interest in enabling themselves to maintain a diary and select the history in the form of data, in order to take appropriate measures in critical situations.

SUMMARY OF THE INVENTION

Therefore, in accordance with the invention, a data processing device is proposed for processing measured values from an analysis or measurement device with the characteristics of claim 1, and also a method of operating a data processing device with the characteristics of claim 12. The analysis or measurement device can be any device with which medically relevant data and measurement values are collected, e.g. a blood glucose measurement device. For simplicity, the bulk of this disclosure describes the present invention in the context of diabetics, diabetes diagnostics, and blood glucose monitoring and measurements. This is not intended to limit the scope of the invention or the claims appended hereto, as will be appreciated by a person of ordinary skill in the art.

The invention generally enables even visually impaired and visually impaired diabetics, in a simple manner, to maintain a diary about the development of their blood glucose levels and to select data sets from the large saved data volume, for purposes of, e.g., finding identical or similar situations from the past and comparing the physiological reaction of the past situation with the present situation and taking appropriate measures. To measure the blood glucose level, a conventional blood glucose measurement device can be employed, which is configured for use by visually impaired diabetics. The measurement values collected by the conventional blood glucose measurement device are transmitted by means of a data input interface to the data processing device of the present invention. The data input interface can therefore be provided by means of a cable or can be wireless. Wireless variants are widely known amongst professionals. Examples of such are infrared interfaces, radio interfaces, Bluetooth interfaces etc.

After carrying out a measurement with a blood glucose measurement device, the result of the measurement is transmitted to the data processing device of the present invention. The data processing device audibly emits the result of the measurement and the associated basic data set. The basic data set comprises the time and date of the measurement and the acquired blood glucose level. Alternatively, a plurality of measurements can be carried out and stored in the blood glucose measurement device before they are transmitted to the data processing device. After the transmission of one or more basic data sets, they are automatically saved in the data processing device.

According to the invention, a user can manually input further physiological parameters such as insulin quantities, carbohydrate exchange, etc. via the input unit (e.g. a numerical keypad of the input unit) and additionally save them to a basic data set which e.g. has been transmitted automatically. The size of the memory unit is chosen such that the data processing device can save a sufficient number of such data sets to enable a detailed diary to be constructed. For example the size of the memory unit may be selected such that many thousands of such data sets can be saved. With the modern availability of technologies, it is even possible to construct a memory unit which can save many tens of thousands of such data sets.

By means of an input unit, a user of the data processing device can select the desired data set from the multitude of saved data sets. According to the invention, the selection can be carried out in such a way that the user uses the input unit to input, for each parameter of the basic data sets, target ranges and time interval limits respectively. The intersections of the inputted targets for the different parameters provide a search cluster according to which the search is carried out. Basically, both "AND" search functions and "OR" search functions of individual parameters can be selected. So for example, a user of the device can carry out a target search for the parameters date and insulin value from all data sets between 21 Apr. 2006 and 25 Sep. 2006 with insulin levels above 20 IU (international units).

The data sets acquired in such a way can be audibly output. In this way, a visually impaired user is able to access diary entries by means of a voice output from individually selected data, and thereby is actually able to access a selected data volume from a large quantity of data. Seeing users can also benefit from this. In order to make the output of the data for marking and identifying of selected results easier for the user to ascertain, each selected data set can be receded by an audible signal for delimitation/differentiation against co-selected data sets (secondary data sets) which precede or succeed the selected results. Therefore the invention also comprises a voice output device with a data processing device according to the present invention.

The input unit of the data processing device according to the present invention comprises a forward key and a back key for control of a virtual cursor. By means of these keys, the visually impaired user can navigate within the selected data sets. By means of the forward and back keys of the input unit, the user can access previous and subsequent data sets from the selected set preceded by an audible indication signal. These so-called secondary data sets are not preceded by an audible signal. By means of these selection methods, which represent a second selection in the sense of the present invention, the user can reconstruct the historical and chronological development of the measurement values immediately before and immediately after the aforementioned selected data set. In order for the user to distinguish the different levels of the voice output, the secondary data sets are not preceded by an audible signal. Alternatively, the secondary data sets can be preceded by a different audible signal than the selected data set. Using this modality, the visually impaired user of the data processing device according to the invention has the opportunity to identify physiological conditions in the past, which are similar to the present, and to carry out or optimize the steps taken at that time (the steps taken at that time are reproducible by means of the additional saved physiological parameters). In a still further alternative embodiment, a second audible signal is used for marking different time intervals in which the virtual cursor is moved.

The invention permits the visually impaired user to effectively navigate within an electronic diary comprising many data sets. Each data set comprises many data set fields. In the case of a blood glucose measurement device, a so-called basic data set can consist of the data set fields date, time and blood glucose level. In addition to the data set fields of the basic data sets, further additional data set fields can be provided, which are freely usable by the user. In the case of a blood glucose measurement device, the additional data set fields may in particular be physiological parameters, such as insulin quantities and carbohydrate units. The invention provides the visually paired user with several possibilities to navigate within the extensive data set portfolio. A first possibility consists in retrieving the available data sets in chronological order. This can be carried out by pressing the forward and back keys respectively. For example, by pressing the back key, the most recent data set in the entire data set portfolio can be selected and audibly output. By pressing the back key again, the data set lying chronologically immediately before is then selected and audibly output) and so on. By pressing the forward key, the opposite occurs and the oldest data set in the data set portfolio can be selected and audibly output; by pressing the forward key again, the second oldest data set, and so on. By holding down the corresponding key, a jump function can be activated, which has the effect that the next data set output is the data set which is selected and audibly output a preset or adjustable time interval from the last data set. The time interval or jump can be e.g. one day, two days, a week, 14 days, a month etc. Different time intervals/jumps can be marked by different audible signals.

A second possibility for navigation comprises searching for a physiological parameter/condition. Physiological parameters can be freely entered by a user in definable data set fields or predetermined fields provided for this purpose. In order to design the functionality of the data processing device to be as easy as possible for a visually impaired user, the data processing device has only numerical keys and no letter keys. Thereby, the user defines specific physiological parameters, such as e.g. insulin quantities, or other keywords such as e.g. "sport" or "after lunch" through corresponding code numbers. The act of selecting then involves the user activating the selection function with an associated key (e.g. the forward/backward key) and subsequently interactively inputting a selection criterion after a corresponding prompt from the data processing device. The selection criterion is a parameter such as "sport", which is input by a corresponding code number by which it is defined. After input of the code number and, if necessary, pressing a corresponding confirmation key, the selection is dealt with by the calculation unit of the data processing device and all data sets with a data set field entry "sport" are selected. By pressing a recall key and also the forward and back keys respectively, the user can let the individually selected data sets be successively output audibly.

The data sets are typically preceded by the audible output e.g. a particular audible signal. With a corresponding assigned key, e.g. a cursor key or a left/right key or forward/backward key, the data sets chronologically next to each selected data set can be accessed. These so-called secondary data sets would then not be preceded by an audible signal. Alternatively, these so-called secondary data sets can be preceded by a second audible signal, which is distinct from the first audible signal. These secondary data sets are useful for representing the history of the selected data sets. The user therefore has the possibility of identifying past physiological states that are similar to the current one and then re-initiating or optimizing the steps taken at that time.

Finally, a further possibility for navigation is the input of target ranges, i.e. interval limits for different parameters. This interval selection can be carried out via input of interval limits for one data set field or via input of interval limits for multiple data set fields. For example, a date interval can be entered as a target range, whereupon all data sets lying within the input date interval are selected. Additionally, an interval can still be input for e.g. insulin quantities, which has the result that all data sets within a particular time period with particular insulin values are selected. This enables any desired combination of all target ranges of all parameters and thus an individual and comprehensive navigation of the visually impaired user through the entire data portfolio.

According to the present invention, the data processing device typically provides the user with selection possibilities in response to the first selection to enable a medically relevant second selection. The selection options for a second selection can comprise calculation of an average of the data sets retrieved from the first selection, an insulin quantity administered within a particular time period, extreme values of glucose levels within the data sets retrieved from the first selection, an amount of hypo- or hyperglycaemia before or after the data sets determined through the first selection occurring within a particular time period, or Occurrences associated with the data sets determined by the first selection.

The hyper- and hypoglycemia can be defined individually and depending on specific additional information associated with the glucose measurement levels, such as e.g. lunch, is approximately <60 ml/dl for hypoglycemia and >180 mg/dl for hyperglycaemia.

It can be provided that an audible output is made for basically all data set fields of a data set, and not just the data set fields on the basis of which the particular selection was made. In this way the user is in a position to evaluate the information in the particular context.

It can further be provided that the first and the second selections are logically combined with each other via an "AND" search function.

Additionally the user can also be offered further functions as selection or search options, e.g. an export of the selected data sets over USB (universal serial bus), Bluetooth or IR (infrared interface), a movement of the data sets in the diary, an audible output only of the data set fields on the basis of which selection was made, combination of the first and second selections using an "OR" search function, further individual logic functions of individual data set fields, or a correction/change to data sets already saved.

It can of course be provided that further selections can be made after the second selection, and the user is also therefore provided with such further selection options.

The described options for input by means of the input unit, and for navigation within the selected data sets are, of course, also used to retrieve the second and potentially further selections.

The invention also comprises a computer program with program code, which can execute a method for carrying out the present invention when the computer program runs on an appropriate calculation unit, e.g. a data processing device with a calculation unit. The computer program can be stored as so-called embedded software on a data processing device; it can, however, also be transferred via an appropriate interface from an appropriate medium onto the data processing device.

BRIEF DESCRIPTION OF THE DRAWINGS

Further advantages and embodiments of the invention arise from the description and the enclosed drawings. The invention is described in more detail below on the basis of illustrative embodiments. However, the invention is not limited to the illustrative embodiments given here. The illustrative embodiments are shown schematically in the figures. Identical reference numbers in the individual figures designate elements which are identical or whose functions are identical, or which correspond to one another in terms of their function.

DETAILED DESCRIPTION OF EMBODIMENTS OF THE PRESENT INVENTION

It is understood that the aforementioned and the following exemplified characteristics are applicable not only in the specified combination, but also in other combinations or in isolation, without departing from the scope of the present invention.

Figure 1:
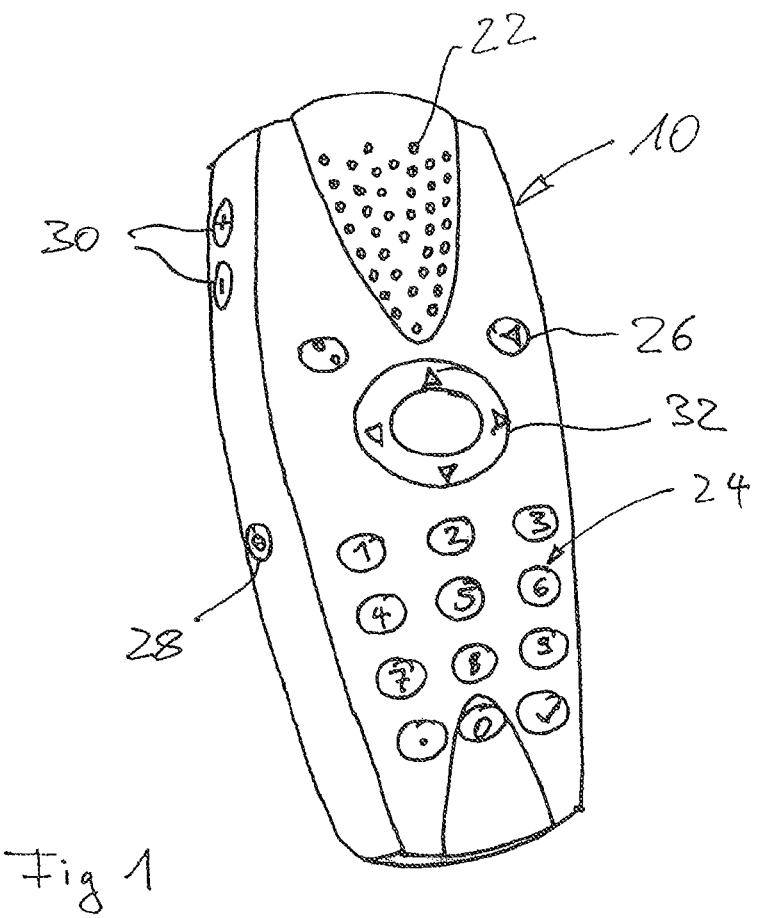
FIG. 1 shows a perspective view of an exemplary embodiment of a data processing device according to the present invention.
Figure 2:
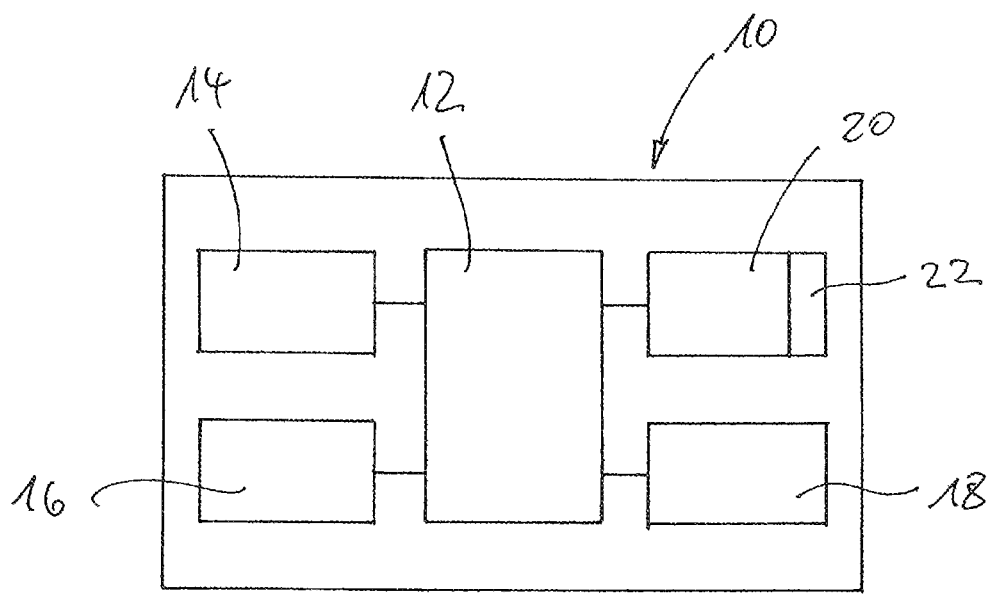
FIG. 2 illustrates a block diagram view of the layout of the embodiment of the data processing device shown in FIG. 1.

A data processing device 10 according to the present invention, formed as a voice output device, is shown in FIG. 1 in perspective representation and in a schematic block diagram in FIG. 2.

The data processing device 10 comprises a calculation unit 12, a first memory unit 14, a second memory unit 16, an input unit 18 and an output unit 20 with an audible data output interface 22. The audible data output interface 22 in certain embodiments can be, e.g., a loudspeaker (see FIG. 1) a connector for head-phones, and/or a connector for earphones.

In certain embodiments, the data processing device 10 further comprises a plurality of keys (which comprise component parts of the input unit 18), with which an operator can operate and use the data processing device 10. In one embodiment, the keys comprise a numeric keypad 24 (e.g. arranged in the style of a telephone in the exemplary embodiment shown) and may further comprise components such as control keys 32 (arrow keys), input confirmation key 26, on/off key 28, +/− keys 30 for volume control among other things. It is understood that the form of the input unit and in particular the style and size of the keypad are not limited to the illustrated embodiment and the specialists also take into account other forms of keypad arrangement.

In other embodiments, the input unit further comprises one or more (not shown), interfaces for data input, such as e.g. an infrared interface, a serial data interface and/or a USB interface. Alternatively an e.g. Bluetooth interface or similar can also be provided.

In one embodiment, the first memory unit 14 is configured for storing/saving audio files from which audible (e.g. voice) output of the data processing device can be generated (as described in the parallel European patent application number 06 025 798.7 which is incorporated herein by reference in its entirety).

In other embodiments, the second memory unit 16 is configured for storing/saving data sets forming a data set portfolio, which are at least partially based on meteorologically collected data. In the example of a medical data processing device, the data sets can originate from a blood glucose measurement device or another medical measurement device and be transferred to the data processing device of the present invention by means of an appropriate interface (as previously described) and stored there in the second memory unit 16. Such a data set, which is meteorologically collected and transferred from an external device, is described as a basic data set within the scope of this application. A basic data set comprises at least two data set fields. For example a basic data set in the field of blood glucose measurement may comprise three: data set fields, the date and time of the measurement value acquisition and also the measured blood glucose level.

A basic data set can be automatically stored in the second memory unit 16 after transfer and output via the audible data output interface 22 (e.g. loudspeaker).

Furthermore, the data processing device according to yet other embodiments of the present invention offers the user the option to define further data set fields himself and to input values, data or other details which are important and relevant to him. These values, data or other details can be, e.g., further physiological parameters such as insulin quantities, carbohydrate units etc. Additionally, details such as "sport", "lunch" or similar can be input. Thereby, the visually impaired user is provided the possibility to maintain a diary about the development of his health condition.

The data set portfolio of such a medical diary will typically comprise a high number of data sets after a period of use. To enable a visually impaired user to navigate within the data set portfolio and to make the contents accessible to him (and also to enable him to analyse his electronic medical diary), according to embodiments of the present invention, an interactive two tier selection of data can be provided, which conforms to the requirements of a visually impaired person. The selection therefore takes place by e.g. contents of data set fields that are to be selected.

The visually impaired user can, for example, according to embodiments of the present invention, audibly retrieve data sets in chronological selection by pressing a corresponding key, e.g. correlating forward and back keys (arrow keys 32). Through a single operation (e.g. a short press) of the back key (e.g. left arrow) the data set with the most recent date and time is selected and audibly output. The audible output itself can take place according to one of the voice output methods already known to specialists or according to the method of the applicant, as described in the parallel European patent application number 06 025 798.7.

By pressing the back key once more, the next most recent data set is selected and audibly output etc. During the audible output, each data set can, according to embodiments of the present invention, be preceded by a (first) audible signal, e.g. a "ping". If the user wants to obtain an output beginning with the oldest data set, he can do so analogously by pressing the correspondingly assigned key, e.g. the forward key. By pressing both assigned keys as appropriate the data set portfolio can be navigated back and forth in any chronological direction.

In other embodiments, the user can also activate a so-called jump function, with which he selects data sets at a preset or selectable time interval. The time interval ca amount to, e.g., 7 days, 14 days, one month, or longer. The activation of the jump function can be carried out by holding down the assigned key. Of course, other possibilities for activation of the jump function can be provided, such as pressing a function key, by which the function of the correspondingly assigned key (e.g. forward/back key) switches to a jump function mode.

In order to distinguish the output of data sets with the jump function activated from data sets with the jump function inactivated, according to yet other embodiments of the present invention, the data sets with the jump function activated can be preceded by an audible signal which differs from the first audible signal, e.g. in pitch. Because visually impaired users often have developed very sensitive hearing, they can differentiate between the different data sets in this way. Alternatively, different jump functions can be differentiated one from each other by means of different audible signals.

It is understood that other combinations of audible signals can also be chosen, in order to allow a differentiation. So for example, the output in base-mode can be carried out with short strokes of the associated key without a preceding audible signal (a non-audible signal, as it were), whereas with the jump function activated the output is preceded by a signal. Furthermore, it is readily possible for a person of ordinary skill in the art to produce a data processing device with multiple levels of jump function.

In yet other embodiments, a further selection option is the input of target ranges. By this, the input of interval limits, i.e. an interval selection, is understood within the scope of the present invention. During interval selection, an interval and a target range can be input for each parameter (thus each data set field), on the basis of which a selection of the data sets is then carried out. Furthermore a combination of multiple target range inputs is possible, the result of which is then an average of the data sets selected for each parameter target range.

As an example, a selection of all data sets which lie between 21 Jun. 2006 and 4 Oct. 2006 and contain insulin levels over 20 insulin units (IE) will be carried out. This would mean that the user inputs 21 Jun. 2006 and 4 Oct. 2006 as interval limits for the data set field "date" and inputs 20 and unlimited as the interval limits for the data set field "insulin value". The input takes place interactively, controlled through a voice controller (not specifically described here) of the data processing device. In other examples, the interval can be limited to a single value; so for example, by inputting 12:00 for the lower and upper interval limits for the data set field "time" all data sets can be acquired, which were collected at exactly 12:00 midday, if the user wants to select and audibly output his insulin values at this time. If only a lower limit (e.g. 12:00 midday) is input, then all values above that limit (i.e. greater than 12:00) are determined; if the value accordingly input as upper limit only, then all values below that limit (smaller than 12:00) are determined.

In one embodiment, the audible output is performed automatically after the selection is made or after a corresponding key (play-back key) is pressed by the user.

In other embodiments, the audible output of every selected result or data set takes place, for example, with a preceding (first) audible signal.

Embodiments of the invention also allow the user to hear one or more additional medically relevant selections of so-called neighbouring data sets to a selected data set. Within the scope of the present invention, the term 'neighbouring data set' is to be understood as a data set that is not necessarily part of the subset of the data set selection but lies chronologically immediately before or after a selected data set. For example if as in the previous example, all data sets between 21 Jun. 2006 and 4 Oct. 2006 with an insulin value over 20 IU were to be selected, then the first acquired data set (e.g. the oldest or the most recent data set) will be audibly output. After the output of the data set the user can decide whether he wants to audibly output a neighbouring data set, which lies chronologically before or after the output data set. To that end he presses a correspondingly assigned key (e.g. the sideways key left arrow or right arrow). For each selected data set, one or more neighbouring data sets in each chronological direction can be output, e.g. each of the three nearest data sets chronologically before and after the selected data set. These data sets can also be described as secondary data sets of the selected data set. The secondary data sets can be preceded by the output of an audible signal which differs from the first audible signal which precedes the selected data set in order to distinguish between data sets.

The interval selection according to embodiments of the present invention offers the visually impaired user the possibility to identify similar physiological conditions to the current one encountered in the past and, as the ease may be, to listen to the measures taken at that time (which are stored in the individually defined data set fields) and to repeat (or optimize) them.

Other embodiments of the invention offer, as an additional selection option to the user, selection according to the contents of individually defined data set fields. This option of selection can also be referred to as keyword selection or, in the case of a medical data processing device, selection according to physiological parameters/conditions.

As already previously described, the visually impaired user can define data set fields for specific and personally important physiological conditions and then supplement the so-called basic data sets with corresponding inputs in these data set fields. These could be additional declarations such as "sport", "stress" etc. as well as the already named insulin value, which could influence or shape the health condition. For the retrieval of these parameters, keyword selection is used. With the help of the keyword selection, specific terms and declarations in the additional, individually defined, data set fields can be searched. One way of doing this is that after accessing the keyword selection (e.g. interactively through an audible menu or through pressing an assigned key or key combination) the user inputs a numeric code, which is preset or individually defined for the searched term (or the selection can be don-e by placing the virtual cursor on the parameter to be searched and pressing the forward or backward key). The selection, triggered in such a manner, can be successively audibly output, either automatically or by pressing a key, e.g. the forward/back key. For example, if the numeric code "3" is defined for the term "sport", then after entry of the number "3" all data sets which contain the term "sport" (or rather: the number "3" which stands for the term "sport") in a data set field are selected. By pressing e.g. the back key the user will then audibly output the data set from the selected data sets, which has the most recent date. After output of this data set, the user can then press the key again to retrieve the next most recent data set, and so on. It goes without saying that for output of the results of a keyword selection, a jump function mode can be used, and it also goes without saying that for the output of the results of a keyword selection, the option is provided to retrieve secondary data sets (as above).

After the first selection, the user is offered, according to certain embodiments of the present invention, a second medically relevant selection to narrow or widen the result of the first selection. The second selection is such that the user is provided with selection options based on the first selection. The selection options for a second selection can comprise calculation of an average of the data sets retrieved from the first selection, an insulin quantity administered within a particular time period, extreme values of glucose levels within the data sets retrieved from the first selection, an amount of hypo- or hyperglycaemia before or after the data sets determined through the first selection occurring within a particular time period, or occurrences associated with the data sets determined by the first selection.

So it can be, for example, that a user of an embodiment of the present invention, upon making a first selection on the basis of a data set field with the additional information "sport", is offered the option of audibly outputting all data sets which represent hyper- or hypoglycaemic conditions within e.g. 12 hours after measurements associated with "sport". The user can then use the information about administered insulin quantities also stored in this data set to gradually make improvements in their therapy performance, in order to prevent hyper- or hypoglycaemic conditions.

The term "medically relevant" within the scope of this application is also understood to include every procedure which aims to convey a picture to the user which is as accurate and complete as possible about his condition, e.g. his blood glucose condition. In particular the user should be put in a position, on the basis of the targeted stipulation of selection choices, to prevent hyper- or hypoglycaemic conditions.

In connection with the second selection, the user is, of course, also offered the same input and navigation options as those described above.

It is therefore possible to use an embodiment of the present invention to search both according to occurrences of e.g. sport, eating, stress etc. and also according to particular measurement ranges (intervals). With a chronological list of selected data, the data can be worked through in two different modest on the one hand it is possible to skip in single steps from one hit to the next with the cursor key, on the other hand the events can be skipped through in chronological gaps (e.g. weekly) by holding down the cursor key, wherein a second signal sound (second audible signal) precedes in the latter case.

With the embodiments of the present invention, a visually impaired user has the opportunity for the first time to maintain a medical diary independently, with sole responsibility and without external help. He has the opportunity to adjust his blood glucose and to "screen" historical data, i.e. to navigate through the portfolio of such historical data, so that he or she as a visually impaired person can access the data contents without external help. In this way, the visually impaired person can avoid errors in their blood glucose entry and so prevent further health complications. The invention embodiments therefore permit a prompt retrieval of data, which were previously only painstakingly accessible. The prompt retrieval is of great importance, because in critical situations the body must be quickly brought back into balance through provision of the corresponding insulin quantity.

Clearly, the data can be exported over a corresponding interface, either completely or in accordance with a selection, to a computer with an appropriate table program, such that it can there be e.g. screened and evaluated by an attending doctor (recognition of physiological reactions of the user, development of appropriate therapeutic measures).

The features disclosed in the above description, the claims and the drawings may be important both individually and in any combination with one another for implementing the present invention in its various embodiments.

It is noted that terms like "preferably", "commonly", and "typically" are not utilized herein to limit the scope of the claimed invention or to imply that certain features are critical, essential, or even important to the structure or function of the claimed invention. Rather, these terms are merely intended to highlight alternative or additional features that may or may not be utilized in a particular embodiment of the present invention.

For the purposes of describing and defining the present invention it is noted that the term "substantially" is utilized herein to represent the inherent degree of uncertainty that many be attributed to any quantitative comparison, value, measurement, or other representation. The term "substantially" is also utilized herein to represent the degree by which a quantitative representation may vary from a stated reference without resulting in a change in the basic function of the subject matter at issue.

Having described the present invention in detail and by reference to specific embodiments thereof, it will be apparent that modification and variations are possible without departing from the scope of the present invention defined in the appended claims. More specifically, although some aspects of the present invention are identified herein as preferred or particularly advantageous, it is contemplated that the present invention is not necessarily limited to these preferred aspects of the present invention.

What is claimed is:

1. A data processing device for processing measurement values from a medical measurement device, the data processing device comprising:
   an input unit;
   a data input interface configured for communication with the medical measurement device;
   a memory unit for storage of data sets, wherein the data sets are received from the medical measurement device via the data input interface;
   a calculation unit; and
   an audible data output interface configured for communication with a data output unit,
   wherein the input unit is operable by a user to make a first selection of measurement results from the data sets stored in the memory unit and is configured for making a second selection of measurement results from the data sets stored in the memory unit, wherein the audible data output interface is configured to provide an audible output of the measurement results in the first selection made by the user and is preceded by and to provide a first audible signal and is further configured to provide an audible output of the measurement results in the second selection, wherein the audible output for each of the selected measurement results occurs automatically after both the first and the second selection, and wherein the audible output of each first selection and second selection of measurement results is preceded by the first audible signal and a second audible signal, respectively, and the first audible signal has a pitch that is distinct from a pitch of the second audible signal.

2. The data processing device according to claim 1, wherein the audible data output interface comprises at least one of a loudspeaker, a connection for headphones, and a connection for earphones.

3. The data processing device according to claim 1, wherein the input unit comprises at least one of a selection key, a numeric keypad, and arrow keys configured for controlling a virtual cursor.

4. The data processing device according to claim 1, wherein the data input interface comprises a wireless interface for communication with a measurement device.

5. The data processing device according to claim 1, wherein the input unit is configured for making the first selection comprising a chronological selection according to content of a data set field stored in the memory unit, the first selection being selectable by pressing an assigned key on the input unit.

6. The data processing device according to claim 1, wherein the input unit is configured for making the first selection comprising a keyword selection being selectable using the input unit by inputting of a numeric code standing for a keyword forming a particular selection criterion according to content of a data set field stored in the memory unit.

7. The data processing device according to claim 1, wherein the input unit is configured for making the first selection comprising an interval selection being selectable using the input unit by inputting interval limits for a data set field stored in the memory unit in which the selection should be made.

8. The data processing device according to claim 1, wherein the second selection comprises one of the selection options selected from the group consisting of: a calculation of an average of the measurement results retrieved by the first selection from the memory unit, an insulin quantity administered within a particular time period, extreme values of glucose levels within the measurement results included in the first selection from the memory unit, an amount of hypo- or hyperglycaemia before or after the measurement results included in the first selection from the memory unit occurring within a particular time period, and occurrences associated with the measurement results determined by the first selection from the memory unit or/and the output of secondary data.

9. The data processing device according to claim 1, wherein the device is configured for a user to browse through the selected data sets stored in the memory unit by means of the input unit.

10. A method of processing measurement values from a medical measurement device, comprising the steps of:
   a) providing a data processing device comprising:
      a data input interface for receiving the measurement values from the medical measurement device,
      a calculation unit and a memory unit for receiving, processing and storing the measurement values from the measurement device as one or more data sets,
      an input unit operable by a user that is configured for making selections of one or more data sets from the data sets stored in the memory unit,
      a data output unit, and
      an audible data output interface configured for communication with the data output unit;
   b) communicating the measurement values from the medical measurement device to the data processing device and storing them in the memory unit as one or more data sets;
   c) making a first selection of measurement values from the stored data sets via user operation of the input unit; and
   d) generating an audible output of the measurement values selected by the user in the first selection using the audible data output interface, the audible output of each selected data set being preceded by a first audible signal,
   wherein the data processing device further comprises a jump function associated with the memory unit, and further comprising the steps of activating the jump function for selecting new measurement values having selectable chronological gaps therebetween and, after activating the jump function, generating a second audible signal with a pitch distinct from a pitch of the first signal and producing an audible output of the new measurement values.

11. The method according to claim 10, wherein providing the data processing device includes providing the data processing device with the audible data output interface comprising at least one of a loudspeaker, a headphone connection and an earphone connection.

12. The method according to claim 10, wherein providing the data processing device includes providing the data processing device with the input unit comprising at least one of a selection key, a numeric keypad, and arrow keys configured for controlling a virtual cursor, and wherein the first selection comprises particular measurement values corresponding to a selection option selected from the group consisting of a chronological selection, a keyword selection made by inputting a numeric code standing for a keyword forming a selection criterion, and an interval selection made by inputting interval limits for a data set field from which the selection is desired to be made.

13. The method according to claim 10, further comprising the step of making a second selection based on the measurement values within the first selection, wherein selection options for the second selection being selected from the group consisting of: a calculation of an average of the measurement values retrieved by the first selection, an insulin quantity administered within a particular time period, extreme values of glucose levels within the measurement values retrieved by the first selection, an amount of hypo- or hyperglycaemia before or after the measurement values determined through the first selection occurring within a particular time period, occurrences associated with the measurement values determined by the first selection, and the output of secondary data.

14. The method according to claim 10, further comprising the step of browsing through the measurement values of the first selection in chronological order.

15. The method according to claim 10, wherein the data processing device is configured for choosing to have the measurement values of the first selection audibly output chronologically forward or backward.

16. A data processing device for processing measurement values from a medical measurement device, the data processing device comprising:
    an input unit;
    a data input interface configured for communicating with the medical measurement device;
    a memory unit for storing data sets, wherein the data sets are received from the medical measurement device via the data input interface;
    a calculation unit; and
    an audible data output interface configured for communicating with a data output unit,
    wherein the input unit is operable by a user to make a first selection of measurement results from the data sets stored in the memory unit, wherein the audible data output interface is configured to provide an audible output of the measurement results in the first selection made by the user and is preceded by and to provide a first audible signal, wherein the memory unit and the input unit are configured with a jump function activatable by the user, the jump function configured for selecting data sets from the memory unit having a desired time interval, and wherein the audible data output interface is further configured to produce a second audible signal before the occurrence of an audible output of data sets selected according to the jump function, the second audible signal having a pitch that is distinct from a pitch of the first audible signal.

17. The data processing device according to claim 16, wherein the audible data output interface comprises at least one of a loudspeaker, a connection for headphones, and a connection for earphones.

18. The data processing device according to claim 16, wherein the input unit comprises at least one of a selection key, a numeric keypad, and arrow keys configured for controlling a virtual cursor.

19. The data processing device according to claim 16, wherein the data input interface comprises a wireless interface for communicating with the measurement device.

20. The data processing device according to claim 16, wherein the input unit is configured for making the first selection comprising a chronological selection according to content of a data set field stored in the memory unit, the first selection being selectable by pressing an assigned key on the input unit.

21. The data processing device according to claim 16, wherein the input unit is configured for making the first selection comprising a keyword selection being selectable using the input unit by inputting of a numeric code standing for a keyword forming a particular selection criterion according to content of a data set field stored in the memory unit.

22. The data processing device according to claim 16, wherein the input unit is configured for making the first selection comprising an interval selection being selectable using the input unit by inputting interval limits for a data set field stored in the memory unit in which the selection should be made.

23. The data processing device according to claim 16, wherein the input unit is configured for making a second selection of measurement results from the data sets stored in the memory unit, and wherein the audible data output interface is configured to provide an audible output of the measurement results with the second selection.

24. The data processing device according to claim 23, wherein the second selection comprises one of the selection options selected from the group consisting of: a calculation of an average of the measurement results retrieved by the first selection from the memory unit, an insulin quantity administered within a particular time period, extreme values of glucose levels within the measurement results included in the first selection from the memory unit, an amount of hypo- or hyperglycaemia before or after the measurement results included in the first selection from the memory unit occurring within a particular time period, and occurrences associated with the measurement results determined by the first selection from the memory unit or/and the output of secondary data.

25. The data processing device according to claim 23, wherein the audible voice output for each of the selected measurement results occurs automatically after both the first and the second selection, and wherein the audible output of each first selection and second selection of measurement results is preceded by the first audible signal and a second audible signal, respectively, and the first audible signal has a pitch that is distinct from a pitch of the second audible signal.

26. The data processing device according to claim 16, wherein the device is configured for a user to browse through the selected data sets stored in the memory unit by means of the input unit.

* * * * *